United States Patent [19]

Arakawa et al.

[11] 4,147,848

[45] Apr. 3, 1979

[54] PROCESS FOR PURIFICATION OF ISOPRENE

[75] Inventors: Masatoshi Arakawa; Haruo Yamanouchi; Taro Okumura; Teruo Yoshida, all of Yokkaichi, Japan

[73] Assignee: Japan Synthetic Rubber Co. Ltd., Tokyo, Japan

[21] Appl. No.: 860,595

[22] Filed: Dec. 14, 1977

[30] Foreign Application Priority Data

Dec. 20, 1976 [JP] Japan .................... 51-153026

[51] Int. Cl.$^2$ .................... C08F 136/08; C07C 7/04; C07C 11/18
[52] U.S. Cl. .................... 526/77; 260/681.5 R; 526/340.2
[58] Field of Search .................... 526/77, 340.2; 260/681.5 R

[56] References Cited

U.S. PATENT DOCUMENTS

| 3,285,901 | 11/1966 | Forman | 526/340.2 |
| 3,442,878 | 5/1969 | Gippin | 526/77 |
| 3,549,721 | 12/1970 | Sholtis et al. | 260/681.5 R |
| 3,583,966 | 6/1971 | Davison | 526/77 |
| 3,635,931 | 1/1972 | Davison | 526/77 |
| 3,784,626 | 1/1974 | Ginnasi et al. | 260/681.5 R |
| 3,851,010 | 11/1974 | Rescalli et al. | 260/681.5 R |
| 3,860,496 | 1/1975 | Ginnasi et al. | 260/681.5 R |
| 3,947,506 | 3/1976 | Lybarger | 260/681.5 R |
| 3,980,528 | 9/1976 | Rescalli et al. | 260/681.5 R |

*Primary Examiner*—Alan Holler
*Attorney, Agent, or Firm*—Cooper, Dunham, Clark, Griffin & Moran

[57] ABSTRACT

A process for purifying a crude isoprene containing polymerization inhibiting materials such as acetylenes and sulfur compounds to produce high purity or polymerization grade isoprene comprising distilling the crude isoprene in the presence of at least one member selected from saturated hydrocarbons containing 6 to 8 carbon atoms, withdrawing the polymerization inhibiting materials as an overhead fraction and obtaining purified isoprene as a bottom fraction.

13 Claims, 4 Drawing Figures

PROCESS FOR PURIFICATION OF ISOPRENE

BACKGROUND OF THE INVENTION

1. Field of the Invention

This invention relates to a process for purifying crude isoprene. More particularly, it is concerned with a process for the removal of polymerization inhibiting materials such as acetylenes, sulfur compounds and the like contained in crude isoprene which is separated by known procedures such as extractive distillation or liquid-liquid extraction from the $C_5$ hydrocarbon fraction obtained by pyrolysis or dehydrogenation of hydrocarbons.

2. Description of the Prior Art

Isoprene is a starting material for production of polycis-1,4-isoprene useful as synthetic rubber, and recently it has been increasingly important. While various procedures have been proposed to produce isoprene, a method of separating and purifying isoprene contained usually in an amount of 10 to 20% in a $C_5$ hydrocarbon fraction obtained by pyrolysis of hydrocarbons is commercially employed as one of the most economical procedures for the production of isoprene.

This $C_5$ hydrocarbon fraction contains paraffins, olefins, diolefins, acetylenes and the like as well as isoprene. Furthermore, it contains a small amount of sulfur compounds resulting from organic sulfur compounds present as impurities in hydrocarbon feeds. Since many of these compounds have boiling points quite close that of isoprene or form azeotropic mixtures with isoprene, it is very difficult to separate and purify isoprene by conventional procedures. For the separation and purification of isoprene, extractive distillation and liquid-liquid extraction using polar solvents such as acetonitrile, dimethylformamide, N-methyl pyrrolidone and the like are known.

Even with these procedures, however, it is difficult to obtain high purity isoprene containing no polymerization inhibiting materials, suitable for use in the production of polyisoprene. Among the polymerization inhibiting materials, cyclopentadiene, acetylenes and sulfur are known to be especially harmful. therefore, it is quite important to minimize the concentration of these impurities to such an extent that they do not interfere with the polymerization of isoprene.

Various procedures have been proposed to remove acetylenes. For example, the azeotropic distillation process utilizing isopentane as described in Japanese Patent Publication No. 7664/1960, a method of adsorbing on a molecular sieve as described in Japanese Patent Publication No. 6202/1960, the extractive distillation process utilizing polar materials such as acetonitrile, dimethylformamide and the like as described in Japanese Patent Publication Nos. 26485/1968 and 41323/1972, the selective hydrogenation process as described in Japanese Patent Publication No. 22324/1970, a method of treating with alkali metals such as sodium and the like described in British Pat. No. 1070893 are known. These procedures, except for the azeoptropic distillation process utilizing isopentane; however, are not effective in removing 2-butyne. This azeoptropic distillation process also suffers from the disadvantage in that recycling and reuse of isopentane involve some difficulty, and it is not always an economical procedure.

On the other hand, for removal of dimethyl sulfide or other sulfur compounds having boiling points quite close to that of isoprene, several procedures have been proposed. For example, the azeotropic distillation process utilizing isopentane described in Japanese Patent Publication No. 7664/1960, and the method of treating with a solution of a silver salt in a polar solvent described in Japanese Patent Laid Open No. 83302/1975, and others, are known. The azeotropic distillation process utilizing isopentane, however, has disadvantages in that it is difficult to separate isopentane because it is liable to form an azeotropic mixture with dimethyl sulfide and in that recycling and reuse of isopentane involve some difficulty. Therefore, it is not always an economical procedure. The method of treating with a solution of a silver salt in a polar solvent has the defect that the silver salt is expensive. In addition, this procedure has the disadvantage that acetylenes usually present in crude isoprene together with dimethyl sulfide easily form silver acetylides, resulting in the formation of the quite desirable conditions for stable operation.

SUMMARY OF THE INVENTION

An object of this invention is to provide a process for purifying a crude isoprene which removes the above described prior art disadvantages.

Another object of this invention is to provide a process for removing polymerization inhibiting materials such as acetylenes, sulfur compounds and the like contained in a crude isoprene.

A further object of this invention is to provide a process for removing acetylenes and/or sulfur compounds contained in a crude isoprene to such an extent that they do not interfere with the polymerization of isoprene.

Another object of this invention is to provide a process for producing high purity or polymerization grade isoprene suitable for use with polymerization catalysts such as Ziegler based catalysts, lithium based catalysts and the like.

Another object of this invention is to provide a process for carrying out purification of isoprene and polymerization of purified isoprene in one system.

Other and further objects of this invention will become apparent from the detailed description.

It has now been found that these objects are attained by distilling a crude isoprene in the presence of at least one member of a specific saturated hydrocarbon group which does not form an azeotropic mixture with any of acetylenes, sulfur compounds and isoprene, that is, distillation of a crude isoprene in the presence of such a specific saturated hydrocarbon increases the relative volatilities of the acetylenes and sulfur compounds to isoprene and enables the easy removal of these impurities to such an extent that they do not interfere with the polymerization of isoprene.

This invention provides a process for purifying a crude isoprene containing polymerization inhibiting materials such as acetylenes and sulfur compounds which comprises distilling the crude isoprene together with at least one member selected from saturated hydrocarbons containing 6 to 8 carbon atoms, withdrawing the polymerization inhibiting materials as an overhead fraction and obtaining purified isoprene as a bottom fraction.

DETAILED DESCRIPTION OF THE INVENTION

Figure 1:
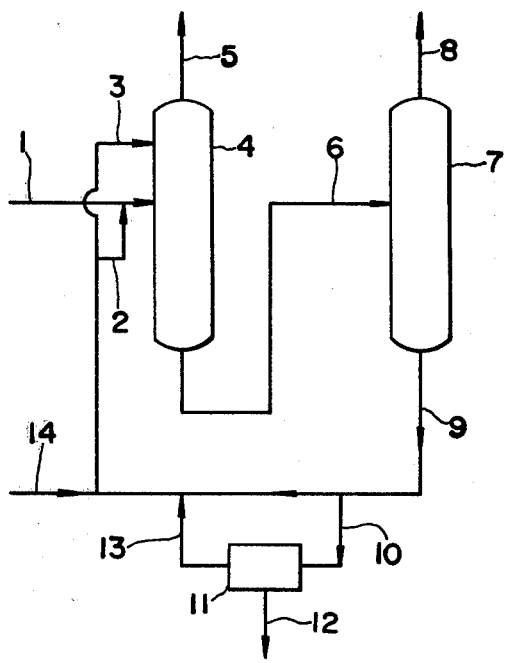
FIG. 1 illustrates a flow diagram showing one embodiment of this invention.

The term "polymerization inhibiting materials" used in this invention designates those compounds present as constituents of crude isoprene which have a boiling point ranging from about 25° C. to 38° C., which is close to that of isoprene (34.08° C.), and which adversely affect its polymerization.

Typical examples of these polymerization inhibiting materials are acetylenes and sulfur compounds. Representative examples of the acetylenes are 3-methyl-1-butyne (b.p. 26.35° C.), 2-butyne (b.p. 26.99° C.), 2-methyl-1-butene-3-yne (b.p. 32.50° C.) and the like. Representative examples of the sulfur compounds are dimethyl sulfide (b.p. 37.3° C.), ethyl mercaptan (b.p. 37° C.) and the like.

The process of this invention is applicable to a variety of crude isoprenes, for example, crude isoprene obtained by concentrating a $C_5$ hydrocarbon fraction by procedures such as extractive distillation and the like, the $C_5$ hydrocarbon fraction being obtained by pyrolysis of hydrocarbons such as naphtha and the like, crude isoprene obtained by concentrating by the same procedures as described above a $C_5$ hydrocarbon fraction produced by dehydrogenation or oxidative dehydrogenation of isopentane contained in a petroleum fraction, and the like can be employed.

These crude isoprenes contain usually 20 to 100 ppm of dimethyl sulfide, 20 to 200 ppm of ethyl mercaptan, 100 to 1,000 ppm of 3-methyl-1-butyne, 1 to 5% of 2-butyne, and 0.1 to 2% of 2-methyl-1-butene-3-yne, each being based on the weight of isoprene, although these values may vary depending upon the kind of a hydrocarbon feed employed, the process employed, etc. Since the boiling points of these impurities are close to that of isoprene, it is very difficult to separate isoprene from them by commonly employed distillation procedures.

The addition of the saturated hydrocarbons of this invention permits easy removal of the impurities by conventional distillation procedures to such an extent that they do not interfere with the polymerization of isoprene. For example, it is possible to decrease the sulfur compounds to less than about 20 ppm and the acetylenes to less than about 50 ppm. Furthermore, if the distillation conditions are made more rigorous, it is possible to decrease the sulfur compounds to less than about 10 ppm and the acetylenes to less than about 20 ppm.

Isoprene from which the polymerization inhibiting materials have been removed to the above extent can be satisfactorily employed as a monomer for polymerization in the presence of a Ziegler catalyst, a lithium based catalyst or the like.

The saturated hydrocarbons of this invention, which are added to increase the relative volatilities of the acetylenes and sulfur compounds contained in crude isoprene to isoprene and to reduce the impurities content to an extent that they do not interfere with the polymerization of isoprene, are aliphatic and alicyclic hydrocarbons containing 6 to 8 carbon atoms, and mixtures thereof.

Representative examples of these saturated hydrocarbons containing 6 to 8 carbon atoms are, for example, n-hexane, 2-methylpentane, 3-methylpentane, 2,2-dimethylbutane, 2,3-dimethylbutane, n-heptane, 2-methylhexane, 3-methylhexane, 3-ethylpentane, 2,2-dimethylpentane, 2,3-dimethylpentane, 2,4-dimethylpentane, 3,3-dimethylpentane, 2,2,3-trimethylbutane, n-octane, 2-methylheptane, 3-methylheptane, 2,2-dimethylhexane, 2,3-dimethylhexane, 2,5-dimethylhexane, 3,4-dimethylhexane, 2,2,3-trimethylpentane, 2,2,4-trimethylpentane (isooctane), 2,3,3-trimethylpentane, 2,3,4-trimethylpentane, cyclohexane, methylcyclopentane, methylcyclohexane, ethylcyclopentane, 1,1-, 1,2-, and 1,3-dimethylcyclopentane, ethylcyclohexane, 1,2-, 1,3- and 1,4- dimethylcyclohexane, isopropylcyclopentane and the like.

These saturated hydrocarbons can be used alone or in combination with each other. When they are used as mixtures, it is preferred to employ those mixtures having a relatively narrow boiling point range.

The saturated hydrocarbons used in the invention are normally commercially available as industrial solvents, and for other uses. Representative examples include hexane (95%), hexane (75%), mixed hexane, isohexane, methylpentane, heptane, mixed heptane, industrial heptane, isoheptane, industrial heptane, octane, mixed octane, isooctane, methylcyclopentane, cyclohexane, methylcyclohexane, and the like, and mixtures thereof, as described in Koki Ishibashi, Ed., *Yozai Binran* (*Handbook of Solvents*), 3rd Ed., Maki Syoten, Tokyo (1964).

Preferred saturated hydrocarbons are n-hexane, n-heptane, mixed heptane and mixed octane.

Hydrocarbons other than saturated hydrocarbons containing 6 to 8 carbon atoms are, surprisingly, not suitable for use in this invention. For example, hydrocarbons containing 5 carbon atoms such as isopentane, n-pentane and the like are not suitable because they form an azeotropic mixture with at least one of isoprene, acetylenes and sulfur compounds. Referring to isopentane, for example, it does not form an azeotropic mixture with isoprene, but it forms azeotropic mixtures with 2-butyne, 3-methyl-1-butyne, and dimethyl sulfide. Therefore, it is difficult to separate isopentane from these compounds. Additionally, there is the economic problem that it is difficult to recycle and reuse the isopentane. Since n-pentane forms an azeotropic mixture not only with 2-methyl-1-butene-3-yne, dimethyl sulfide and the like, but also with isoprene, the separation of isoprene from n-pentane is very difficult, resulting in a reduction in the purity and recovery of isoprene.

Saturated hydrocarbons containing 4 carbon atoms such as n-butane, isobutane and the like are also not suitable for use in this invention from the economic standpoint. The reason for this is that since the vapor pressure of the saturated hydrocarbons containing 4 carbon atoms is higher than that of isoprene, the amount of heat energy consumed is large as compared with those for the saturated hydrocarbons of this invention because all of the saturated hydrocarbons have to be condensed in an overhead condenser.

Saturated hydrocarbons containing not more than 3 and not less than 9 carbon atoms are useful for removing the acetylenes and sulfur compounds, but they are not suitable for use in this invention for the following reasons. That is, in carrying out the process of this invention industrially, it is preferred that the vapor in the top of a distillation tower is in the state that it can be condensed by industrial water, cooled water from a cooling tower, sea water and the like. From this requirement, the pressure at which the distillation tower is operated must be controlled so that the overhead temperature is more than 20° C., preferably more than 40° C. When a saturated hydrocarbon containing not more than 3 carbon atoms is employed to meet with the above requirement, the bottom temperature will be inevitably more than 120° C. As a result, problems such as loss of isoprene due to polymerization, plugging of pipes and the like take place. In addition, the same problem as described above in connection with $C_4$ hydrocarbons takes place with these lower hydrocarbons. On the other hand, when a saturated hydrocarbon containing at least 9 is employed, the temperature of the system is excessively high at the step where isoprene and the saturated hydrocarbon are separated, although the bottom temperature does not always exceed 120° C.

In distilling a crude isoprene containing the polymerization inhibiting materials such as the acetylenes and sulfur compounds in the presence of the above described saturated hydrocarbons, increasing the concentration of the saturated hydrocarbon in the system enhances the separation of the polymerization inhibiting materials. However, if the concentration is excessively increased, the total amount being treated increases and the apparatus cost markedly increases. Furthermore, the energy required for the separation increases. These are not desirable from the standpoint of commercial production. Thus the saturated hydrocarbons of this invention are maintained at about 10 to 90 mole %, preferably 10 to 70 mole % in the liquid phase of the distillation system.

The saturated hydrocarbons of this invention may be introduced at the feed point of the crude isoprene or at an appropriate point above the feed point in the distillation tower. The saturated hydrocarbon is withdrawn from the bottom of the tower together with isoprene, whereas the polymerization inhibiting materials are withdrawn from the top of the tower as an overhead fraction. The bottom fraction comprising the saturated hydrocarbon and isoprene is introduced into a saturated hydrocarbon recovering zone where the saturated hydrocarbon is separated from isoprene and recycled to the distillation zone which in this instance is shown as a tower.

While the distillation conditions are not especially limited, the distillation is usually carried out under the conditions of: overhead pressure about 0 to 5 Kg/cm$^2$G, overhead temperature about 20° to 70° C., and bottom temperature about 50° to 120° C. The presently preferred conditions are overhead pressure 0.5 to 3 Kg/cm$^2$G, overhead temperature 40° to 55° C. and bottom temperature 70° to 110° C. If the overhead pressure is appreciably below the above lower end of the range, the condensation of the overhead fraction may become difficult. This is not desirable from the economic standpoint. On the other hand, if the overhead pressure is appreciably above the range, the temperature of the system unnecessarily increases, with resulting problems such as the loss of isoprene due to polymerization, plugging of pipes and the like.

The recovery of the used saturated hydrocarbon for recycling and reuse is usually carried out by distillation. When the bottom fraction comprising the saturated hydrocarbon and isoprene is distilled in the recovering zone, the isoprene leaves the zone as an overhead fraction and the saturated hydrocarbon is withdrawn from the bottom and recycled to the distillation tower.

Hereinafter, this invention will be explained in detail by reference to the accompanying drawings.

Referring to FIG. 1, a crude isoprene containing a small amount of acetylenes and sulfur compounds as impurities is fed through line 1 to distillation tower 4 at the intermediate part thereof. A saturated hydrocarbon is fed through line 2 and/or line 3 to an inlet for introduction of the crude isoprene and/or the upper portion above the distillation tower, respectively. The crude isoprene is thus distilled in the presence of the saturated hydrocarbon in distillation tower 4.

The acetylenes and sulfur compounds are recovered from the top of distillation tower 4 through line 5 to the outside of the system. A mixture of isoprene and the saturated hydrocarbon is withdrawn from the bottom of the tower through line 6 and fed to saturated hydrocarbon recoverying tower 7. From the top of saturated hydrocarbon recoverying tower 7, purified isoprene is recovered through line 8. The saturated hydrocarbon is withdrawn through line 9 from the bottom of the tower and recycled to distillation tower 4 through line 2 and/or line 3.

During the recycling of the saturated hydrocarbon, heavy materials such as polymer oils and the like gradually accumulate. Therefore, a portion or the whole of the recycling stream is fed to saturated hydrocarbon refining zone 11 through line 10. The heavy materials are discharged out of the system through line 12, and the saturated hydrocarbon so refined is returned to the recycling system through line 13. If necessary, a fresh saturated hydrocarbon is introduced into the system through line 14 to compensate for the loss of the circulating saturated hydrocarbon.

Figure 2:
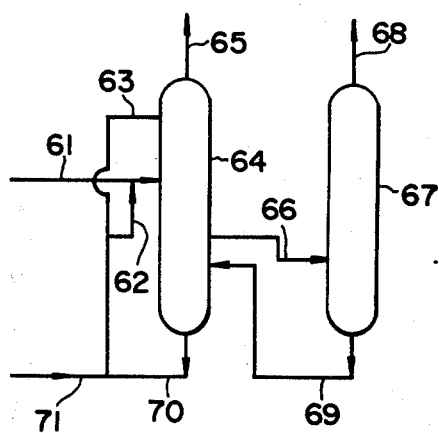
FIG. 2 illustrates a flow diagram showing another embodiment of this invention.

FIG. 2 illustrates another embodiment of the process of this invention. Referring to FIG. 2, a crude isoprene feed containing polymerization inhibiting materials such as acetylenes and sulfur compounds is fed through line 61 to distillation tower 64 at the intermediate portion thereof. A saturated hydrocarbon is fed through line 62 and/or line 63 to distillation tower 64 at an inlet for introduction of the crude isoprene and at a position above the inlet respectively. Thus, distillation of the crude isoprene feed is carried out in the presence of the saturated hydrocarbon.

The polymerization inhibiting materials are recovered through line 65 out of the system. A side stream comprising a polymerization inhibiting material-free isoprene and the saturated hydrocarbon is withdrawn through line 66 located below the inlet for the crude isoprene and fed to distillation tower 67. From the top of the distillation tower through line 68 is obtained a purified isoprene. A bottom fraction comprising the saturated hydrocarbon and a lower concentration of isoprene is withdrawn through line 69 and returned to distillation tower 64 at a lower portion thereof. As in the embodiment of FIG. 1, although not shown in FIG. 2, a portion of a recycling stream may be passed through saturated hydrocarbon refining zone to remove the heavy materials, and if necessary, a fresh saturated hydrocarbon is supplied through line 71.

Figure 3:
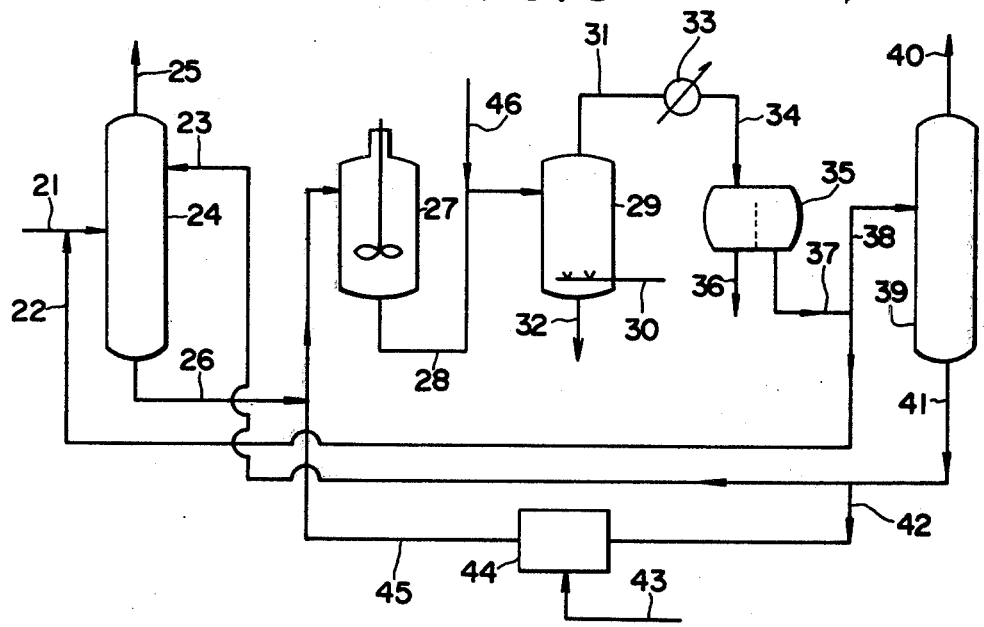
FIG. 3 illustrates a flow diagram showing another embodiment in which purification of a crude isoprene and polymerization of a purified isoprene are carried out in a combined system.

FIG. 3 illustrates one embodiment of this invention in which purification of a crude isoprene and polymerization of purified isoprene are combined together.

Polyisoprene containing the cis-1,4 bond in a high ratio is formed by polymerizing isoprene in a non-polar solvent in the presence of the so-called Ziegler catalyst as described in Japanese Patent Publication No. 32313/1972. Of the impurities contained in an isoprene feed, the acetylenes are materially completely consumed by the catalyst. However, since almost all of demethyl sulfide remains unconsumed, its concentration in the unreacted isoprene increases. On the other hand, saturated hydrocarbons such as n-hexane and the like are often employed as non-polar solvents for the polymerization of isoprene. Therefore, by combining the purification step of a crude isoprene and the polymerization step of isoprene as shown in FIG. 2 excellent effects can be obtained.

Referring to FIG. 3, a crude isoprene containing a small amount of acetylenes and/or sulfur compounds is fed through line 21 to distillation tower 24 at the intermediate portion thereof. A mixture of the unreacted isoprene, which has been recovered from the polymerization step and contains a relatively high concentration of sulfur compounds, and a polymerization solvent comprising a saturated hydrocarbon such as n-hexane is fed to the intermediate portion of distillation tower 24 through line 22. (The isoprene concentration is usually 2 to 10% by weight although it varies depending upon the ratio of solvent and the degree of reaction of isoprene at the polymerization step.) The polymerization solvent, saturated hydrocarbon separated in depentanizer 39 is fed from line 23 to distillation tower 24 at a position located above an inlet for introduction of an isoprene feed. Thus, distillation is carried out in the presence of the saturated hydrocarbon in distillation tower 24.

The acetylenes and sulfur compounds contained in the crude isoprene feed and the recycling isoprene are withdrawn from the top of distillation tower 24 through line 25 to the outside of the system. The isoprene, refined to such an extent that it does not inhibit the polymerization, and the saturated hydrocarbon are withdrawn from line 26 and introduced into polymerization reactor 27. To polymerization reactor 27 is fed a catalyst prepared in polymerization catalyst preparing zone 44 through line 45, and the polymerization is carried out therein. The reaction mixture is introduced into stripper 29 through line 28, in which the unreacted isoprene and the saturated hydrocarbon are separated from isoprene polymer by steam fed through line 30, and they are sent to condenser 33 through line 31. The isoprene polymer is converted into an aqueous slurry by water fed through line 46, withdrawn from the bottom of stripper through line 32 and sent to polymer finishing zone (not shown) wherein it is formed into solid rubber.

In condenser 33, the vapor of the unreacted isoprene and the saturated hydrocarbon, and steam are condensed and sent through line 34 to decanter 35 in which an excess of water is withdrawn out of the system through line 36. The unreacted isoprene and the saturated hydrocarbon are withdrawn through line 37. One portion of the mixture is fed through line 38 to depentanizer 39 and the remainder is recycled through line 22 to distillation tower 24.

In depentanizer 39, a small amount of $C_5$ olefins, and cyclopentadiene contained in the crude isoprene feed are withdrawn from the top of the tower through line 40 together with the isoprene in order to keep these impurities at lower levels, and they are usually sent to a monomer plant for repurification. On the other hand, the saturated hydrocarbon containing no isoprene is withdrawn from the bottom through line 41. One portion of the saturated hydrocarbon is recycled through line 42 to catalyst preparing unit 44 and the remainder is recycled through line 23 to distillation tower 24. A catalyst component is fed through line 43 to catalyst preparing unit 44, diluted with the saturated hydrocarbon and supplied through line 45 to polymerization reactor 27.

Figure 4:
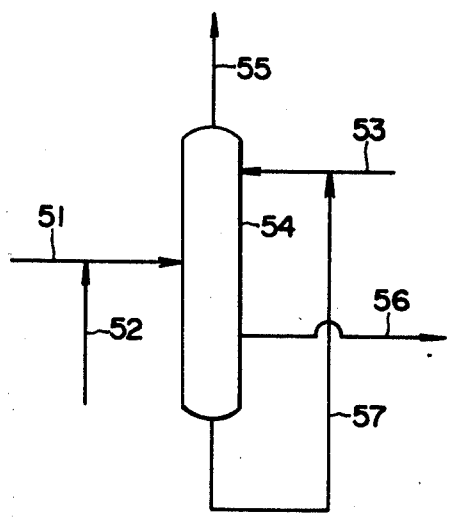
FIG. 4 illustrates a flow diagram showing one embodiment of the process of FIG. 3.

FIG. 4 illustrates another embodiment of the process shown in FIG. 3. In FIG. 3, the operation load of depentanizer 39 is determined by the amount of olefins, cyclopentadiene and the like, which are contained in the crude isoprene feed fed through line 21 and which cannot be consumed at the polymerization step, or by the amount of by the saturated hydrocarbon needed for operating distillation tower 24. The latter amount is often a factor determining the load. By arranging distillation tower 24 of FIG. 3 in the manner shown in FIG. 4, it is possible to secure the amount of the saturated hydrocarbon required.

A crude isoprene containing a small amount of acetylenes and/or sulfur compounds is introduced through line 51 into distillation tower 54 at the intermediate point thereof. A mixture of the unreacted isoprene and a polymerization solvent comprising a saturated hydrocarbon such as n-hexane, which has been recovered from the polymerization step, is fed through line 52 (corresponding to line 22 in FIG. 3) to distillation tower 54 at the intermediate point thereof. The polymerization solvent, saturated hydrocarbon separated in depentanizer 39 shown in FIG. 3 is fed through line 53 (corresponding to line 23 in FIG. 3) to the distillation tower 54 at the position above the feed point of the crude isoprene feed.

The saturated hydrocarbon containing substantially no isoprene is withdrawn from the bottom of the tower and recycled to the top section of the tower through line 57. Thus, the distillation is carried out in the atmosphere of the saturated hydrocarbon in distillation tower 54. The acetylenes and sulfur compounds contained in the crude isoprene feed and the recycling isoprene are withdrawn from the top of the tower through line 55 to the outside of the system. On the other hand, the isoprene, refined to such an extent that the impurities contained therein exert no bad influence on the polymerization, and the saturated hydrocarbon are withdrawn from distillation tower 54 at the position below the inlet for the crude isoprene feed through line 56. They are then supplied to polymerization reactor 27 shown in FIG. 3.

Amongst the particular advantages of this invention, the following are the most prominent:

(1) The polymerization inhibiting materials such as acetylenes and sulfur compounds contained in crude isoprene can be easily removed by a conventional distillation procedure to such an extent they do not interfere with the polymerization of isoprene.

(2) The saturated hydrocarbons containing 6 to 8 carbon atoms for use in this invention are industrially available easily and cheaply. Furthermore, since they can be easily separated from other components, it is possible to recycle and reuse them. This is greatly advantageous from the economic standpoint.

(3) By combining a purification step and a polymerization step of isoprene, and employing the same solvent, it is possible to effect the purification and polymerization of isoprene continuously and effectively.

The following non-limiting examples are given by way of illustration only.

In the examples, all percents are by mole unless otherwise indicated.

Relative volatility is given by the following equation:

$$\text{Relative volatility} = \frac{X_1 \times Y_2}{X_2 \times Y_1}$$

$X_1$: Concentration of isoprene in liquid phase (%)
$Y_1$: Concentration of isoprene in vapor phase (%)
$X_2$: Concentration of component to be measured in liquid phase (%)
$Y_2$: Concentration of component to be measured in vapor phase (%)

Vapor-liquid equilibrium under atmospheric pressure was measured by the use of a vapor-liquid equilibrium measuring apparatus of Rose Williams modified type (produced by Kyowa Kagaku K.K., Japan).

EXAMPLE 1

To a mixture of 98% of isoprene, 1% of dimethyl sulfide and 1% of ethyl mercaptan was added n-hexane in various proportions. The resulting liquid mixtures were charged to the vapor-liquid equilibrium measuring apparatus and measured in vapor-liquid equilibrium under atmospheric pressure by a conventional procedure. It was considered that equilibrium was reached after 2 hours from the beginning of circulation of the liquid from the vapor phase zone by heating the vessel. For comparison, the mixture to which no n-hexane was added was tested in the same manner.

The results obtained are shown in Table 1.

TABLE 1

| Concentration of n-Hexane in Liquid Phase (%) | Relative Volatility | |
|---|---|---|
| | Dimethyl Sulfide | Ethyl Mercaptan |
| 0 | 1.042 | 1.320 |
| 15.0 | 1.090 | 1.426 |
| 34.5 | 1.225 | 1.830 |
| 48.5 | 1.280 | 1.890 |
| 58.5 | 1.270 | 1.875 |
| 79.0 | 1.362 | 1.945 |

EXAMPLE 2

| | Amount (wt %) |
|---|---|
| 1,4-Pentadiene | 4.5 |
| 2-Butyne | 4.5 |
| C$_5$ Olefins | 1.5 |
| 2-Methyl-1-butene-3-yne | 1.0 |
| Isoprene | 88.1 |
| Dimethyl Sulfide | 0.2 |
| Ethyl Mercaptan | 0.2 |

To a crude isoprene having the above composition was added n-hexane in various proportions. The resulting liquid mixtures were charged to the vapor-liquid equilibrium measuring apparatus and measured in vapor-liquid equilibrium under atmospheric pressure by a conventional procedure. For comparison, the crude isoprene to which no n-hexane was added was tested in the same manner.

The results obtained are shown in Table 2.

TABLE 2

| Concentration of n-Hexane in Liquid Phase (%) | Relative Volatility | | | |
|---|---|---|---|---|
| | 2-Butyne | 2-Methyl-1-butene-3-yne | Dimethyl Sulfide | Ethyl Mercaptan |
| 0 | 1.268 | 1.115 | 1.050 | 1.325 |
| 10.2 | 1.340 | 1.184 | 1.091 | 1.420 |
| 29.0 | 1.355 | 1.235 | 1.185 | 1.783 |
| 52.0 | 1.456 | 1.340 | 1.315 | 1.880 |
| 72.5 | 1.500 | 1.432 | 1.398 | 1.950 |
| 82.5 | 1.520 | 1.457 | 1.413 | 1.937 |

EXAMPLE 3

This example was conducted according to the embodiment shown in FIG. 1.

To distillation tower 4 having 120 plates, at the 80th plate from the bottom thereof was fed through line 1 2,787 Kg/hr of a crude isoprene feed having the following composition

| | Amount (wt %) |
|---|---|
| 1,4-Pentadiene | 4.5 |
| 2-Butyne | 4.5 |
| C$_5$ Olefins | 1.5 |
| 2-Methyl-1-butene-3-yne | 1.0 |
| Isoprene | 88.5 |
| Dimethyl Sulfide | 20 ppm |
| Ethyl Mercaptan | 20 ppm |

A total of 5,263 Kg/hr of a mixed heptane having the composition as shown below was fed through line 3 (line 2 was closed) to distillation tower 4 at the 115th plate from the bottom thereof.

| Mixed Heptane | Amount (%) |
|---|---|
| n-Heptane | 35.2 |
| 2-Methylhexane | 21.7 |
| 3-Methylhexane | 14.3 |
| 3-Ethylpentane | 4.5 |
| 2,2-Dimethylpentane | 6.3 |
| 2,3-Dimethylpentane | 7.7 |
| 2,4-Dimethylpentane | 3.1 |
| 3,3-Dimethylpentane | 4.0 |
| 2,2,3-Trimethylbutane | 3.2 |

The crude isoprene feed was thus distilled in the presence of the mixed heptane. The vapor effluent from the top of the tower was condensed in a condenser (not shown), and 15,200 Kg/hr of the condensate was returned to the top as reflux. A fraction comprising principally 1,4-pentadiene, acetylenes and sulfur compounds was discharged out of the system through line 5 in a rate of 334 Kg/hr. The heat energy needed for operating distillation tower 4 was supplied from a reboiler (not shown) provided at the bottom of the tower. The conditions under which the tower was operated were as follows: pressure 1.1 Kg/cm$^2$G, overhead temperature 51.1° C., and bottom temperature 92.8° C.

From the bottom of distillation tower 4 was withdrawn 7,716 Kg/hr of an effluent consisting of 2,506 Kg/hr of an isoprene fraction free of the impurities and 5,210 Kg/hr of the mixed heptane. This was fed through line 6 to mixed heptane recovering tower 7 where the saturated hydrocarbon was to be recovered. The vapor effluent from the top of mixed heptane recovering tower 7 was condensed in a condenser (not shown). A portion of the condensate was returned as reflux to the top of the tower in a rate of 1,480 Kg/hr, and 2,455 Kg/hr of the remainder was withdrawn through line 8 as a purified isoprene effluent.

The composition of the purified isoprene effluent was as follows:

|  | Amount |
| --- | --- |
| 1,4-Pentadiene | 100 ppm |
| 2-Butyne | <5 ppm |
| $C_5$ Olefins | 0.5 wt % |
| 2-Methyl-1-butene-3-yne | 50 ppm |
| Isoprene | 99.4 wt % |
| Dimethyl Sulfide | <5 ppm |
| Ethyl Mercaptan | <5 ppm |
| Mixed Heptane | 0.1 wt % |

The heat energy needed for operating distillation tower 7 was supplied from a reboiler (not shown) provided at the bottom thereof.

From the bottom of distillation tower 7 was obtained 5,260 Kg/hr of the mixed heptane containing about 1% of isoprene through line 9. A fresh mixed heptane was added through line 14 to compensate the loss of the mixed heptane, and the resulting mixture was recycled through line 3 to distillation tower 4.

A portion of the recycling hexane is passed through purifying zone 11 to remove heavy materials comprising isoprene dimer.

EXAMPLE 4

This example was conducted according to the embodiment shown in FIG. 3. In this example, a crude isoprene having the following composition was employed.

|  | Amount |
| --- | --- |
| Isoprene | 99.0 wt % |
| $C_5$ Olefins | 0.9% |
| Cyclopentadiene (CPD) | 1 ppm |
| Dimethyl Sulfide (DMS) | 40 ppm |
| 2-Butyne | 200 ppm |
| 2-Methyl-1-butene-3-yne | 500 ppm |

To distillation tower 24 having 110 plates, at the 28th plate from the bottom thereof, were fed 3,371 Kg/hr of the crude isoprene feed and 12,635 Kg/hr of a recycling isoprene flow consisting of 833 Kg/hr of isoprene (containing 80 ppm of DMS and 15 ppm of CPD), 135 Kg/hr of C5 olefins and 11,667 Kg/hr of n-hexane, respectively, through line 21 and line 22. On the other hand, 2,820 Kg/hr of n-hexane materially free of isoprene was fed through line 23 to distillation tower 24 at the 108th plate from the bottom thereof. The crude isoprene was thus distilled in the atmosphere of n-hexane.

The vapor effluent from the top of the tower was condensed in a condenser (not shown), and 24,500 Kg/hr of the condensate was returned to the top of the tower as reflux. 5 Kg/hr of isoprene rich in acetylenes and DMS was taken out of the system together with 3 Kg/hr of n-hexane through line 25. Thus, purified isoprene suitable for use in polymerization was obtained from the bottom of the tower through line 26. The impurities contained in this purified isoprene were as follows:

|  | Amount (ppm) |
| --- | --- |
| Dimethyl Sulfide (DMS) | 20 |
| Cyclopentadiene | 4 |
| Acetylenes | 40 |

18,818 Kg/hr of a stream consisting of 4,169 Kg/hr of the purified isoprene, 165 Kg/hr of $C_5$ olefins and 14,484 Kg/hr of n-hexane was combined with 200 Kg/hr of a polymerization catalyst solution from line 45 and fed to polymerization reactor 27. A mixture of tributylaluminum, titanium tetrachloride and diphenyl ether fed through line 43 was mixed with 200 Kg/hr of n-hexane fed through line 42 in catalyst preparation unit 44 and it was supplied through line 45 to polymerization reactor 27.

In polymerization reactor 27, the polymerization was conducted at 50° C. for 5 hours in a conversion of about 75%. The reaction products were withdrawn from the reactor as an n-hexane solution together with unreacted hexane and fed through line 28 to stripper 29. To this stripper 29 were fed water and steam through lines 46 and 30 respectively. The stream fed to stripper 29 was separated into a polymer slurry containing 3,127 kg/hr of isoprene polymer and a mixture of unreacted isoprene and the solvent. The polymer slurry was fed through line 32 to polymer finishing zone (not shown) where a solid polymer was obtained. The unreacted isoprene and n-hexane were withdrawn from line 41 together with the steam, and this stream was condensed in condenser 33 and fed to decanter 35. In this decanter, an excess of water was withdrawn through line 36. Thus, from line 37 was obtained 15,891 Kg/hr of a stream consisting of 1,042 Kg/hr of isoprene (containing 80 ppm of DMS and 15 ppm of CPD), 165 Kg/hr of $C_5$ olefins and 14,684 Kg/hr of n-hexane. Of this stream, 12,635 Kg/hr portion was recycled through line 22 to distillation tower 24 as a recycling isoprene stream, and the remainder, 3,256 Kg/hr was fed through line 38 to depentanizer 39.

From the top of depentanizer 39 was withdrawn 240 Kg/hr of a stream consisting of 209 Kg/hr of isoprene (containing 80 ppm of DMS and 15 ppm of CPD), 30 Kg/hr of $C_5$ olefins and 1 Kg/hr of n-hexane through line 40. This stream was sent to monomer purification zone (not shown). From the bottom of depentanizer 39 was obtained 3,016 Kg/hr of n-hexane free of isoprene. Of this n-hexane, 200 Kg/hr portion was sent through line 42 to catalyst preparation zone 43 and the remainder, 2,816 Kg/hr was recycled through line 23 to distillation tower 24 after being supplied with 4 Kg/hr of a fresh n-hexane from a line (not shown). The conditions under which the distillation tower was operated were as follows: operating pressure 0.7 Kg/cm²G, overhead temperature 51.0° C. and bottom temperature 79.4° C.

EXAMPLE 5

This example was conducted according to an embodiment shown in FIG. 4.

The amounts and compositions of streams flowing in lines 51, 52, 53, 55 and 56 were the same as in lines 21, 22, 23, 25 and 26 of Example 4. Distillation tower 54 had 65 plates. Streams in lines 53 and 57 were fed to distillation tower 54 at the 63th plate from the bottom thereof, and a stream in line 56 was withdrawn from the 8th plate from the bottom. 14,240 Kg/hr of an overhead vapor was condensed and returned to the top of the tower.

A stream of 7,250 Kg/hr consisting of 72 Kg/hr of isoprene and 7,178 Kg/hr of n-hexane was withdrawn through line 57 and recycled to the 63th plate from the bottom, in order to increase the concentration of n-hexane in the distillation tower.

In this way, it was possible to further reduce the number of the plates required for the distillation tower and the amount of the reflux. The conditions under which the distillation tower was operated were as follows: overhead pressure 0.7 Kg/cm$^2$G, overhead temperature 50.9° C. and bottom temperature 84.7° C.

EXAMPLE 6

The procedure of Example 3 was repeated with the exception that a mixed hexane having the following composition was employed in place of the mixed heptane.

|  | Amount (%) |
| --- | --- |
| n-Hexane | 18.7 |
| 2-Methylpentane | 23.3 |
| 3-Methylpentane | 27.2 |
| 2,2-Dimethylbutane | 18.5 |
| 2,3-Dimethylbutane | 12.3 |

The amount of a stream flowing in line 3 was 5,320 Kg/hr, and the composition of an effluent from line 8 was as follows:

|  | Amount |
| --- | --- |
| 1,4-Pentadiene | 110 ppm |
| 2-Butyne | <5 ppm |
| C$_5$ Olefins | 0.5% |
| 2-Methyl-1-butene-3-yne | 45 ppm |
| Isoprene | 99.4% |
| Dimethyl Sulfide | <5 ppm |
| Ethylmercaptan | <5 ppm |
| Mixed Hexane | 0.2% |

The conditions under which distillation tower 4 was operated were as follows: overhead pressure 1.1 Kg/cm$^2$G, overhead temperature 51.8° C. and bottom temperature 79.6° C.

EXAMPLE 7

The procedure of Example 3 was repeated with the exception that a mixed octane having the composition shown below was employed in place of the mixed heptane.

|  | Amount (%) |
| --- | --- |
| n-Octane | 18.6 |
| 2-Methylheptane | 17.4 |
| 3-Methylheptane | 12.6 |
| 2,2-Dimethylhexane | 9.7 |
| 2,3-Dimethylhexane | 7.6 |
| 2,5-Dimethylhexane | 4.5 |
| 3,4-Dimethylhexane | 8.2 |
| Isooctanes (2,2,3-trimethylpentane, 2,3,3-trimethylpentane, 2,3,4-trimethylpentane) | 21.4 |

The amount of a stream flowing in line 3 was 5,015 Kg/hr, and the composition of an effluent from line 8 was as follows:

|  | Amount |
| --- | --- |
| 1,4-Pentadiene | 95 ppm |
| 2-Butyne | <5 ppm |
| C$_5$ Olefins | 0.5% |
| 2-Methyl-1-butene-3-yne | 48 ppm |
| Isoprene | 99.4% |
| Dimethyl Sulfide | <5 ppm |
| Ethylmercaptan | <5 ppm |
| Mixed Octane | 0.05% |

The conditions under which distillation tower 4 was operated were as follows: overhead pressure 1.1 Kg/cm$^2$G, overhead temperature 51.7° C. and bottom temperature 95.5° C.

COMPARATIVE EXAMPLE

The procedure of Example 3 was repeated except that no mixed heptane was employed.

Line 3 and line 4 were closed. A crude isoprene was fed through line 1 to distillation tower 4 having 120 plates at the 80th plate from the bottom thereof. An isoprene fraction was withdrawn through line 6. The composition of this isoprene fraction was as follows:

|  | Amount |
| --- | --- |
| 1,4-Pentadiene | 100 ppm |
| 2-Butyne | 50 ppm |
| C$_5$ Olefins | 0.5% |
| 2-Methyl-1-butene-3-yne | 4,000 ppm |
| Isoprene | 99.0% |
| Dimethyl Sulfide | 17 ppm |
| Ethylmercaptan | 13 ppm |

The conditions under which distillation tower 4 was operated were as follows: overhead pressure 1.1 Kg/cm$^2$ G, overhead temperature 52.8° C. and bottom temperature 64.5° C.

From the results given in Examples 3, 6 and 7, and the Comparative Example, it can be seen that the use of the saturated hydrocarbons of this invention permits effective removal of polymerization inhibiting materials contained in a crude isoprene, such as dimethyl sulfide, ethylmercaptan, 2-methyl-1-butene-3-yne, 2-butyne and the like to such an extent that they do not interfere with the polymerization of isoprene with polymerization catalysts such as Ziegler type catalysts, lithium based catalysts and the like.

What is claimed is:

1. A process for purifying a crude isoprene containing polymerization inhibiting material which comprises distilling the crude isoprene in the presence of 10 to 90 mole percent of at least one member selected from the group consisting of saturated hydrocarbons containing 6 to 8 carbon atoms in a first distillation zone withdrawing the polymerization inhibiting materials as an overhead fraction and withdrawing isoprene substantially free of polymerization inhibiting materials as a bottom fraction.

2. A process as in claim 1, wherein the polymerization inhibiting materials are acetylenes and sulfur compounds.

3. A process as in claim 3, wherein the acetylenes are 3-methyl-1-butyne, 2-butyne, and 2-methyl-1-butene-3-yne.

4. A process as in claim 2, wherein the sulfur compounds are dimethyl sulfide and ethylmercaptan.

5. A process as in claim 1, wherein the distillation of the crude isoprene is carried out in the presence of a saturated hydrocarbon selected from the group consisting of n-hexane, n-heptane, mixed heptane and mixed octane.

6. A process as in claim 1, wherein the distillation of the crude isoprene is carried out under the conditions: overhead pressure 0 to 5 Kg/cm$^2$G, overhead temperature 20° to 70° C. and bottom temperature 50° to 120° C.

7. A process as in claim 1, wherein the bottom fraction comprises the isoprene substantially free of polymerization inhibiting materials and the saturated hydrocarbon.

8. A process as in claim 1, wherein the bottom fraction is distilled to separate the saturated hydrocarbon from the isoprene and the saturated hydrocarbon is recycled to the first distillation zone.

9. A process for purifying a crude isoprene containing polymerization inhibiting materials which comprises distilling the crude isoprene in the presence of 10 to 90 mole percent of at least one member selected from the group consisting of saturated hydrocarbons containing 6 to 8 carbon atoms in a first distillation zone under the following conditions: overhead pressure 0 to 5 Kg/cm$^2$G, overhead temperature 20° to 70° C. and bottom temperature 50° to 120° C., withdrawing the polymerization inhibiting materials as an overhead fraction, withdrawing isoprene substantially free of polymerization inhibiting materials and the saturated hydrocarbon as a bottom fraction, and separating the bottom fraction by distillation.

10. A process in accordance with claim 9 in which the saturated hydrocarbon separated from the bottom fraction is recycled to the first distillation zone.

11. A process for purifying a crude isoprene containing polymerization inhibiting materials which comprises distilling the crude isoprene in the presence of 10 to 90 mole percent of at least one member selected from the group consisting of saturated hydrocarbons containing 6 to 8 carbon atoms in a first distillation zone under the following conditions: overhead pressure 0 to 5 Kg/cm$^2$G, overhead temperature 20° to 70° C. and bottom temperature 50° to 120° C. in a first distillation zone, withdrawing the polymerization inhibiting materials as an overhead fraction, withdrawing the saturated hydrocarbon as a bottom fraction and recycling to the first distillation zone, withdrawing a mixture of isoprene substantially free of polymerization inhibiting materials and a lower concentration of the saturated hydrocarbon as a side stream and feeding it to a second distillation zone, distilling the mixture to fractionate it into an isoprene having a still lower concentration of the saturated hydrocarbon and a saturated hydrocarbon, and returning the said saturated hydrocarbon to the first distillation zone.

12. A process for producing polyisoprene from a crude isoprene containing polymerization inhibiting material which comprises the steps of:
  1. introducing the crude isoprene into a first distillation zone wherein the crude isoprene is distilled in the presence of 10 to 90 mole percent of at least one member selected from the group consisting of saturated hydrocarbons containing 6 to 8 carbon atoms under the following conditions: overhead pressure 0 to 5 Kg/cm$^2$G, overhead temperature 20° to 70° C. and bottom temperature 50° to 120° C.,
  2. withdrawing the polymerization inhibiting materials as an overhead fraction and a mixture of isoprene substantially free of polymerization inhibiting materials and the saturated hydrocarbon as a bottom fraction from the first distillation zone,
  3. feeding the said bottom fraction to a polymerization zone wherein the isoprene is polymerized in the saturated hydrocarbon as a non-polar solvent in the presence of a catalyst.
  4. separating the polymerization mixture from the polymerization zone to obtain polyisoprene and a remaining mixture comprising unreacted isoprene and the saturated hydrocarbon,
  5. introducing the remaining mixture into a second distillation zone wherein the remaining mixture is distilled to recover the saturated hydrocarbon as a bottom fraction, and the unreacted isoprene as an overhead fraction, and
  6. recycling the bottom fraction from the second distillation zone to the first distillation zone.

13. A process as in claim 12 wherein the mixture of Step 2 is recovered as a side stream.

* * * * *